US006022831A

United States Patent [19]

Evans

[11] Patent Number: 6,022,831

[45] Date of Patent: Feb. 8, 2000

[54] CONTROL OF ERWINIA AMYLOVORA IN PLANTS

[75] Inventor: Richard R. Evans, Greenville, Miss.

[73] Assignee: BASF Corporation, Mt. Olive, N.J.

[21] Appl. No.: 09/115,134

[22] Filed: Jul. 14, 1998

Related U.S. Application Data

[60] Provisional application No. 60/088,358, Jul. 31, 1997, and provisional application No. 60/112,016, Jul. 15, 1997.

[51] Int. Cl.$^7$ .................... A01N 37/00

[52] U.S. Cl. .................... 504/313; 504/320

[58] Field of Search .................... 504/119, 313, 504/320

[56] References Cited

U.S. PATENT DOCUMENTS

| | | | |
|---|---|---|---|
| 4,560,403 | 12/1985 | Motojima et al. | 71/106 |
| 4,678,496 | 7/1987 | Motojima et al. | 71/76 |
| 4,693,745 | 9/1987 | Brunner | 71/94 |
| 4,866,201 | 9/1989 | Motojima et al. | 560/126 |

OTHER PUBLICATIONS

Sinha and Wood, 1964, Nature 202:824.

Erwin et al., 1979, California Agriculture 33:8–10.

Crossan and Fieldhouse, 1964, Plant Disease Reports, 48:549–550.

Chase et al., 1987, Plant Disease 71:186–187.

Hiremath et al., 1973, Mysore Journal of Agricultural Sciences 7:565–567.

Panduranga Rao and Hiremath, 1986, Indian Phytopath. 39:512–514.

Acta Horticulturae, 1992, 322:293–297.

Acta Horticulturae, 1993, 338:205–215.

Sanders and Soika, 1992, Fungicide and Nematicide Tests 47:300, 47:301 and 47:309.

6th International Symposium on Integrating Canopy, Rootstock and Environmental Physiology in Orchard Systems, Programs and Abstracts, "Enhanced Performance Of Orchard Systems Through Knowledge of Canopy and Rootstock Physiology", Jul. 17–25, 1996 Abstracts Only—pp. 28, 66, 667–671.

PGRSA Quarterly, Plant Growth Regulation Society of America, 24:No. 1 and 2, Jan.–Jun. 1996 (65), (66), (69), (70), (83), (84) Abstracts Only.

Winkler, Reduced risk concept for prohexadione calcium, Integrating Canopy, Rootstocks and Environmental Physiology in Orchard Systems, vol. 2,667–671, 1996.

*Primary Examiner*—S. Mark Clardy
*Assistant Examiner*—Alton Pryor

[57] ABSTRACT

The invention relates to the control of fireblight (*Erwinia amylovora*) in plants by application of acylcyclohexadiones to plants susceptible to fireblight to reduce or prevent the infestation and disease caused by *Erwinia amylovora*. Specific compounds suitable for use in practicing the invention include prohexadione calcium and trinexapac ethyl. Included in the invention are compounds from the formula:

(I)

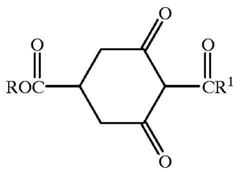

and compounds of the formula (IV)

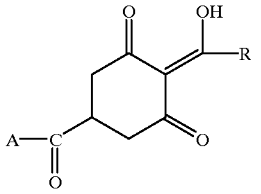

and the metal or ammonium salts thereof.

26 Claims, No Drawings

CONTROL OF *ERWINIA AMYLOVORA* IN PLANTS

CROSS REFERENCE TO RELATED APPLICATIONS

This application claims the benefit of U.S. Provisional Patent Application Ser. No. 60/088,358 filed on Jul. 31, 1997, and U.S. Provisional Patent Application Ser. No. 60/112,016 filed on Jul. 15, 1997.

FIELD OF THE INVENTION

The invention relates to a method of controlling fireblight (*Erwinia amylovora*) on susceptible trees. The invention also relates to the application of acylcyclohexadiones to trees susceptible to fireblight to reduce or prevent the infestation and disease caused by *Erwinia amylovora*. Specific compounds suitable for use in practicing the invention include prohexadione calcium and trinexapac ethyl.

BACKGROUND OF THE RELATED ART

Many bacterial diseases are known which severely affect growth and productivity of many species of cultivated plants. The economic damage caused by such diseases is considerable and effort is put into the control of bacterial diseases For example, in 1991 the effort to control fireblight (*Erwinia amylovora*) in pome fruit (apples and pears) resulted in pesticide applications to an estimated 677,000 product acres. None of the agents currently available to combat bacterial disease in plants are completely satisfactory. Antibiotics and bactericides, such as streptomycin and copper containing pesticides, respectively, normally give limited control. Copper compounds were the first chemicals used commercially for fireblight control. A variety of compounds and formulations are available, including a mixture of copper hydroxide and sulfur (Kocide 101), copper oxychloride sulfate (COCS), and various other inorganic and organic copper compounds. The classic bordeaux mixture has been used extensively. As a group, copper compounds are less effective in controlling fireblight and are more phytotoxic than antibiotics. Most copper compounds cause leaf chlorosis or necrosis and fruit russetting when applied to pear or apple orchards; severity depends on the compound used, timing with respect to stage of growth, formulation and concentration used, and the variety of trees treated.

Antibiotics are antimicrobial compounds that are produced by other microbes. They are produced in quantity either by growth of the organism that synthesizes them or through chemical synthesis. Some have questioned the advisability of using antibiotics for plant protection, because the same materials are sometimes used in human and animal medicine. Widespread use of antibiotics may lead to the development of bacteria that are resistant to the antibiotics; conceivably that resistance may be transferred to bacteria of medical importance.

In order to have a better control of bacterial plant diseases, plant growth regulators, particularly plant growth retardants (i.e., compounds which reduce longitudinal growth), have been investigated on several instances. The degree of success has been relatively limited and very inconsistent. Wilt diseases such as fungal disease on tomato or cotton have been reduced when plants were treated with chlormequat chloride (Sinha and Wood, 1964, Nature 202:824; Erwin et al. 1979, Californian Agriculture 33:8). In other studies chlormequat chloride applications were superior to bactericides for control of Xanthomonas on peppers (Crossan and Fieldhouse, 1964, Plant Disease Reports, 48:549). Likewise, the severity of disease caused by *Pseudomonas, P. syringas pv. hibisci*, by treatment with chloromequat chloride (Chase et al., 1987, Plant Disease 71:186).

Contrasting with above mentioned reports, others have found that the severity of bacterial diseases was increased under the influence of the growth retardant chlormequat chloride: *Xanthomonas malvacearum* in cotton (Hiremath et al., 1973, Myosore Journal of Agricultural Sciences 7:565) and *Xanthomonas campestris pv. vignicola* in cowpea (Panduranga and Hiremath, 1986, Indian Phytopathology 39:512). Likewise, Deckers and Faust (Acta Horticulturae 322:293, 1992) and Deckers and Daemen (Acta Horticulturae 338:205; 1993) presented evidence for an increased susceptibility of pear trees toward infection with fireblight (caused by *Erwinia amylovora*) after being treated with the growth retardants chlormequat chloride, flurprimidol or triazole type compounds.

Others have found that an acylcyclo-hexanedione type plant growth regulator does not suppress fungal diseases in turfgrass. The use of CGA 163935 (trinexepac-ethyl) did not reduce the severity of necrotic ring spot (*Leptosphaeria korrae*) on bluegrass; nor the severity of spring leaf spot (*Drechslera poae*) on bluegrass; nor the severity of Rhizoctonia blight (*Rhizoctonia solani*) on tall fescue (Sanders and Soika, 1992, Fungicide and Nematicide Tests 47:301, 47:300 and 47:309). In the latter two reports, the use of CGA 163935 in combination with the fungicide Banners® was less effective than the fungicide used alone.

Prohexadione belongs to a new family of plant growth regulators (acylcyclohexanedione type plant growth regulators). These growth regulators block the biosynthesis of gibberellin (GA). Gibberellin is mainly responsible for controlling cell elongation. When gibberellin biosynthesis is blocked, plant cells will divide normally but the cells will be shorter. This results in shorter plants (reduced stature). Inhibitors of gibberellin biosynthesis are used in many crops to reduce stature, prevent lodging and the like.

No information to date has been available on the actual effects of this new group of growth retardants, the acylcyclohexanediones, on bacterial plant diseases.

U.S. Pat. No. 4,560,403 describes Prohexadione (3-hydroxy4-propionyl-5-oxo-3-cyclohexene carboxylic acid) and a number of other compounds of a class of cyclohexene plant growth regulators. While the reference does suggest as a general principle that as plant growth regulators all the described compounds could be useful to promote resistance "to phytotoxicity caused by . . . bacterial diseases." It appears that due to the lack of consistent results, both positive and negative, with plant growth regulators; the large number of compounds disclosed in the prior art; the lack of any test data in the reference which would show antibacterial activity; a lack of susceptible organisms and plants disclosed; a lack of effective dosages; that the reference is merely an invitation to experiment to see if resistance can be promoted and not predictive or otherwise of a compound for inducing resistance to bacterial disease for plants.

SUMMARY OF THE INVENTION

It has been discovered that acylcyclohexanedione compounds, their derivatives, and their salts, can be used to control fireblight infection in plants such as in apple and pear trees. Hence, provided herein is a method for the control of fireblight in plants susceptible to fireblight infection, preferably in plants bearing pome fruit such as apples, pears and quince. The method is applicable to the treatment of many plants including but not limited to those plants that comprise the Rosaceae family.

The method comprises applying an effective amount of an acylcyclohexanedione, its derivative, or its pharmacological effective salt to the plant susceptible to fireblight infection. Preferably, the compounds used to practice the invention are applied to a plant susceptible to fireblight infection sufficient to significantly reduce the number of infected branch shoots (disease incidence) or decrease the average canker length (disease severity) caused by exposure of the plant to said fireblight when compared with an untreated plant.

Further provided herein is a combination treatment for control of fireblight comprised of the application of an antibiotic, such as Agrimycin (streptomycin) in combination or sequentially with an effective amount of an acylcyclohexanedione, its derivative, or its pharmacological effective salt to a plant susceptible to fireblight infection, sufficient to significantly reduce the number of infected branch shoots or decrease the average canker length caused by exposure of the plant to said fireblight when compared with an untreated plant.

DETAILED DESCRIPTION OF THE INVENTION

Compounds that may be used to practice particular embodiments of the invention include those described in U.S. Pat. No. 4,560,403, incorporated herein by reference, as represented by the formula:

(I)

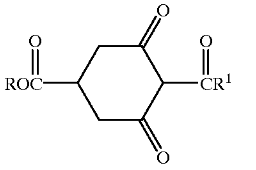

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound.

A preferred compound for use in practicing embodiments of the present invention is prohexadione represented by the formula:

(II)

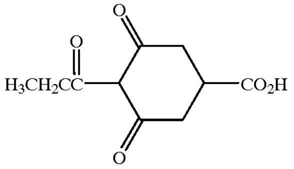

As used herein, prohexadione includes the compound (IUPAC name) 3,5-dioxo-4-propionylcyclohexanecarboxylic acid (or 3,5-dioxo-4-(1-oxopropyl)cyclohexanecarboxylic acid (C.A. name)) and also 3-hydroxy-4-prionyl-5-oxo-3-cyclohexene carboxylic acid and its pharmacological effective salts for example a chloride, sulfate, metrab, acetate, carbonate, hydride, hydroxide, sodium, potassium, calcium, magnesium, barium, aluminum, nickel, copper, manganese, cobalt zinc, iron or silver. The preferred compound for use in preferred embodiments of the invention is prohexadione calcium and is represented by the formula:

(III)

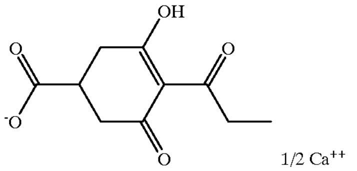

In another aspect of the invention, the method may also be practiced with compounds described in U.S. Pat. No. 4,693,745, incorporated herein by reference, represented by the formula:

(IV)

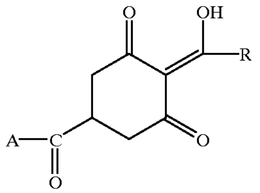

wherein

A is an—$OR_2$ or—$NR_3R_4$ radical,

R is $C_3$–$C_6$ cycloalkyl, $R_2R_3$ and $R_4$ are each independently hydrogen, $C_1$–$C_6$alkyl, $C_1$–$C_6$haloalkyl, $C_2$–$C_{10}$alkoxyalkyl, $C_2$–$C_{10}$alkylthioalkyl, $C_3$–$C_6$alkenyl, which is unsubstituted or substituted by halogen, $C_1$–$C_4$alkoxy or $C_1$–$C_4$alkylthio; $C_3$–$C_6$alkynyl; phenyl or $C_1$–$C_6$aralkyl, wherein the phenyl nucleus is unsubstituted or substituted by halogen, $C_1$–$C_4$alkyl, $C_1$–$C_4$alkoxy, $C_1$–$C_4$haloalkyl, nitro or cyano; one of $R_3$ and $R_4$ is methoxy; or $R_3$ and $R_4$, together with the nitrogen atom to which they are attached, form a 5- or 6-membered heterocyclic ring system which may contain an additional oxygen or sulfur atom in the ring; and the metal or ammonium salts thereof.

Specific compounds of the immediately above noted formula, for use in practicing embodiments of the invention include trinexapac (IUPAC name 4-cyclopropyl(hydroxy)methylene-3,5-dioxyocyclohexanecarboxylic acid) and preferably its ethyl ester, trinexapac-ethyl (IUPAC name, ethyl 4-cyclopropyl(hydroxy)methylene-3,5-dioxocyclohexanecarboxylate; CA name, ethyl 4-(cyclopropylhydroxymethylene)-3,5-dioxyocyclohexanecarbocylate) represented by the formula:

(V)

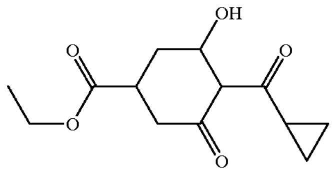

Preferred compounds for use in practicing embodiments of the invention are those that are plant growth regulators that inhibit gibberellin biosynthesis.

As used herein, branch shoots or terminals refer to new growth shoots which form off of old growth on plants. Canker herein refers to the sores (lesions) formed on plants as a result of fireblight infection.

Apple trees refer to the genus trees Malus and include, for example, dessert apple and crabapple type varieties. The invention may be practiced on variety of dessert apple trees including but not limited to Arkansas Black, Baldwin, Beacon, Ben Davis, Braeburn, Burgundy, Cortland, Delicious, Empire, Fuji, Gala, Golden Delicious, Granny Smith, Gravenstein, Grimes Golden, Idared, Jerseymac, Jonafree, Jonagold, Jonamac, Jonathan, Liberty, Lodi, Macoun, McIntosh, Molly's Delicicious, Monroe, Mutsu, Niagara, Nittany, Nothern Spy, Northewestern Greening, Paulared, Priam, Prima, Priscilla, Qunite, Redfree, R. I. Greening, Rome Beauty, Sir Prize, Spartan, Stayman, Summer Rambo, Twenty Ounce, Tydeman Early, Wayne, Wealthy, Winesap, Winter Banana, Yellow Newton, Yellow Transparent, and York Imperial.

The invention may also be practiced on a variety of crabapple trees such as Adirondack, Ames White, Bob White, Centennial, Centurion, Dolgo, Florence, Harvest Gold, Hyslop, Marshall Slender, Naragansett, Omiston Roy, Pink Perfection, Profusion, Red Splendor, Silver Moon, Snowdrift, Spring Snow, Transcendent, White Candle, White Cascade, Whitney, and Winter cold.

Pear trees refer to the genus trees Pyrus and include, for example, dessert pear, asian pear, low chilling pear, and ornamental pear varieties. The invention may be practiced on such variety of dessert pear trees as Aurora, Ayers, Bartlett, Beurre Bosc, Beurre d' Anjou, Beurre Hardy, California, Cascade, Clapp's Favorite, Dawn, DeVoe, Douglas, Doyeene du Comice, Duchesse d'Angouleme, Earlibrite, Flemish Beauty, Forelle, Garber, Gorham, Harrow Delight, Harvest Queen, Highland, Honeysweet, Lincoln, Luscious, Magness, Maxine, Monterey, Moonglow, Packham's Triumph, Rogue Red, Seckel, Sierra, Spartlett, Starkrimson, Tyson, Winter Cole, Winter Nelis, and Worden Seckel,.

The invention may also be practiced on such varieties of asian pear trees as Ar-riang one, Chojuro Imamura aki, Hosui, Ichiban nashi, Ikusankichi, Ishilwase, Kikusui, Kosui, Kumoi, Meigetsu, Nitaka, Nijissekiki, Seigyoku, Seuri, Shinko, Shinseiki, Shinsui, Singo, Tsu Li, and Ya Li.

The invention may also be practiced on such varieties of low chilling pear such as Baldwin, Carnes, Flordahome, Hood, Kieffer, Le Conte, Orient, Pineapple, and Tenn.

The invention may also be practiced on such varieties of ornamental pear as Autumn Blaze, Bradford, Capital, Chanticleer and Whitehouse.

The invention may further be practiced on plants susceptible to fireblight infection such as those belonging to the genera: Cotoneaster, Crataegys, Cydonia, Photinia, Pyracantha, and Sorbus.

The compounds of this invention may be used directly but are more conveniently formulated into compositions for such usage.

The compounds and salts can be applied in a number of ways, for example, they can be applied, formulated or unformulated, directly to the foliage of a tree, or to seeds or to other medium in which the trees are growing or are to be planted, or they can be sprayed on, dusted on, or applied as a cream or paste formulation, or they can be applied as slow release granules.

The compositions may be in the form of dusting powders or granules comprising the active ingredient and a solid diluent or carrier, for example fillers such as kaolin, bentonite, dolomite, calcium carbonate, talc, powdered magnesia, Fuller's earth, gypsum, diatomaceous earth and China clay.

The compositions may also be in the form of dispersible powders, granules or grains comprising a wetting agent to facilitate the dispersion in liquids of the powder or grains which may contain also fillers and suspending agents.

The aqueous dispersions or emulsions may be prepared by dissolving the active ingredient in an organic solvent optionally containing wetting, dispersing or emulsifying agent(s) and then adding the mixture to water which may also contain wetting, dispersing or emulsifying agents(s). Suitable organic solvents are kerosene, cyclohexanone, methylethyl ketone, acetone, methanol, acetonitrile, and the like.

The compositions may also be in the form of liquid preparations for use as dips or sprays which are generally aqueous dispersions or emulsions containing the active ingredient in the presence of one or more of wetting agent(s), dispersing agent(s), emulsifying agent(s) or suspending agent(s). The agents can be anionic or nonionic agents.

The compositions for use as aqueous dispersions or emulsions are generally supplied in the form of a concentrate containing a high proportion of the active ingredient.

The compositions of this invention may usually be formulated into a wettable powder comprising 5 to 95%, preferably 10 to 50% by weight of the new compounds of this invention as active ingredient; 1 to 20%, preferably 5 to 10% by weight of surfactant; and 4 to 44%, preferably 40 to 85% by weight of solid carrier.

The compositions of this invention may be formulated into an emulsifiable concentrate (EC) comprising 5 to 95%, preferably 20 to 70% by weight of the new compound of this invention as active ingredient; 1 to 40%, preferably 5 to 20% by weight of surfactant; and 4 to 94%, preferably 10 to 75% by weight of liquid carrier.

The compositions of this invention may be made up as granules comprising 0.5 to 40%, preferably 2 to 10% by weight of the new compound of this invention as active ingredient; 1 to 20%, preferably 2 to 10% by weight of the surfactant; and 40 to 98.5%, preferably 20 to 96% by weight of solid carrier. And, the compositions of this invention may be formulated into dust comprising 0.5 to 10%, preferably 1 to 5% by weight of the active ingredient; and 99.5 to 90%, preferably 99 to 95% by weight of finely divided solid carrier.

The compositions of this invention may also be formulated into a paste comprising 0.1 to 20%, preferably 1 to 10% by weight of the active ingredient, 1 to 20%, preferably 2 to 10% by weight of surfactant; and 60 to 98.9%, preferably 80 to 97% by weight of paste base.

The rate of application will vary based on the particular tree size and the tree vigor at the time of application. More exact amounts can be determined at the time of use by one skilled in the art. The rate of application of the prohexadione compound of this invention to apple trees may be in the range of 0.0005 kg to 50 kg per hectare and preferably 0.05 kg to 10 kg per hectare as the active ingredient. In particular, when applying the compound of this invention to apple trees, the preferred dosage is from 0.40 kg/ha to 8.0 kg /ha applied as a dilute or concentrated spray by handgun or commercial airblast. When actually applying the prohexadione compositions as a spray, it is usually diluted with water at a concentration of in the range of 5 ppm or up, preferably at about 125–250 ppm.

Trinexapac-ethyl may be applied to apple trees at the same rates as to those described for prohexadione, however preferred rates are up to about 1000 ppm, most preferably from about 500–1000 ppm.

In another aspect of the invention the acylcyclohexanedione compositions may also include an antibiotic for example Streptomycin. Streptomycin which alone gives very little effect but in combination with prohexadione shows additional synergistic activity against fireblight. At the test levels shown effective for apple trees, the prohexadione composition was thought to be ineffective against fireblight in pear trees because previous work with pears treated with an acylcyclohexanedione at an application rate of about 125 to about 250 ppm did not significantly control shoot growth in pear trees that were thought to be disease free.

It has been unexpectedly found that fire blight can be controlled in a pear tree that is susceptible to fire blight wherein the tree is treated with an acylcyclohexanedione. The rate of application of the compounds used in the present invention to pear trees is preferably greater than or equal to about 125 ppm, most preferably between about 125 ppm to about 750 ppm.

The following examples are representative of the invention only and are not intended to be limiting; one skilled in the art will be able to fully practice the invention based on the disclosure and claims, and the examples.

EXAMPLE 1

The calcium salt of Prohexadione was formulated according to the known art. In the following examples, Prohexadione calcium was administered to apple trees (type: Rome, Fuji, Golden Delicious, Jonathan, Red Delicious, and Crab). In addition, the trees were either inoculated with fireblight or left to be exposed to natural fireblight infection. Further, all compounds were applied at a strength of 250 ppm by handgun sprayer at 60 psi and Agrimycin at 0.5 lb ai/100 gal. by dilute handgun. The following results were observed:

TABLE 1

| CALIFORNIA TEST | INOCULATED | Number of Infected Shoots |
|---|---|---|
| 1 Untreated | NO | 9.6 |
| 2 Prohexadione Ca | YES | 3.6 |
| 3 Prohexadione Ca | NO | 2.0 |
| 4 Prohexadione Ca + Agrimycin | YES | 1.0 |
| 5 Prohexadione Ca + Agrimycin | NO | 0.3 |

| VIRGINIA TEST | INOCULATED | % Infected shoots | Average Canker length (cm) |
|---|---|---|---|
| 1 Untreated | YES | 100 | 32.8 |
| 2 Prohexadione Ca | YES | 65 | 18.7 |
| 3 Prohexadione Ca + Agrimycin | YES | 46 | 10.4 |
| 4 Agrimycin | YES | 93 | 31.1 |

EXAMPLE 2

Seedling apples (*Malus domestica*, # MABSD, size #3) were treated with growth regulators prohexadione calcium and trinexapac ethyl (PRIMO®) when new shoot growth measured 5–10 cm. A second application was made two weeks later. Apical shoots were needle inoculated with the *Erwinia amylovora* pathogen three days after the second application on May 3, 1996.

The prohexadione calcium was applied at 50/50 ppm and 100/100 ppm and the trinexapac ethyl (PRIMO®) was applied at 500/500 ppm and 1000/1000 ppm. The spray volume was 935 I/ha (100 GPA) applied with a DeVilbiss sprayer at 20 psi. REGULAID® was used with both growth regulators as an adjuvant at 0.2% v/v. The potting media was METROMIX® 360 soilless potting media.

Plants were grown in a 76/60° F. greenhouse until inoculation with the pathogen. After inoculation plants were transferred to the plant pathology greenhouse set at 78/68° F. with a fog system that delivers a two minute water mist every ten minutes.

The shoot length of the plants were evaluated weekly. Data was reported as shoot growth as percent of check. The results are displayed in Tables 2–4.

TABLE 2

Apple shoot growth following treatment with PROHEXADIONE CALCIUM or TRINEXAPAC-ETHYL

| | | Shoot growth as percent of check | | | |
|---|---|---|---|---|---|
| Compound | Rate ppm ai | 0–7 DAT | 7–14 DAT | 14–21 DAT | 0–21 DAT |
| Untreated | 0 | 100 a | 100 a | 100 a | 100 a |
| Prohexadione | 50/50 | 97 a | 59 b | 85 ab | 74 b |
| Prohexadione | 100/100 | 57 c | 28 c | 71 ab | 35 c |
| trinexapac-ethyl | 500/500 | 62 bc | 18 c | 66 b | 32 c |
| trinexapac-ethyl | 1000/1000 | 64 abc | 12 c | 67 ab | 30 c |
| | CV | 38.11 | 40.09 | 32.78 | 32.12 |

Means followed by the same letter are not significantly different (Duncan's MRT, P = .05).

TABLE 3

Percent of fireblight damage following treatment with PROHEXADIONE CALCIUM or TRINEXAPAC-ETHYL and inoculation with the bacterium *Erwinia amylovora*

| | | Percent fireblight damage | | | |
|---|---|---|---|---|---|
| Compound | Rate ppm ai | 21 DAT | 25 DAT | 31 DAT | 37 DAT |
| Untreated | 0 | 3.5 a | 11.7 a | 32.5 a | 71.7 a |
| prohexadione | 50/50 | 2.8 a | 7.8 ab | 23.8 ab | 50.8 ab |
| prohexadione | 100/100 | 1.2 a | 6.8 b | 29.2 a | 46.7 b |
| trinexapac-ethyl | 500/500 | 1.8 a | 4.3 b | 17.5 ab | 33.3 bc |
| trinexapac-ethyl | 1000/1000 | 0.7 a | 3.2 b | 5.2 b | 16.7 c |
| | CV | 136.87 | 56.94 | 70.71 | 43.77 |

Means followed by the same letter are not significantly different (Duncan's MRT, P = .05).

TABLE 4

Spread of fireblight following treatment with PROHEXADIONE CALCIUM OR TRINEXAPAC and inoculation with the bacterium *Erwinia amylovora*

| | | average canker length in cm per shoot | | | cm canker on 2nd year wood |
|---|---|---|---|---|---|
| Compound | Rate ppm ai | 31 DAT | 34 DAT | 37 DAT | 37 DAT |
| Untreated | 0 | 11.8 ab | 23.8 a | 30.7 a | 6.3 a |
| prohexadione | 50/50 | 28.7 a | 17.3 ab | 21.7 b | 2.0 b |
| prohexadione | 100/100 | 8.5 ab | 12.7 b | 14.8 bc | 1.8 b |
| trinexapac-ethyl | 500/500 | 3.8 ab | 7.8 bc | 11.0 cd | 1.5 b |
| trinexapac-ethyl | 1000/1000 | 1.7 b | 1.8 c | 5.5 d | 0.0 b |
| | CV | 177.65 | 62.22 | 38.04 | 124.11 |

Means followed by the same letter are not significantly different (Duncan's MRT, P = .05).

All growth regulator treatment reduced apple shoot growth as compared to the untreated check (see Table 2). After the 21 DAT date the disease severity was such that shoot growth measurements became meaningless. The 100/100 ppm rate of prohexadione calcium was as effective in reducing shoot growth as the very high rates of trinexapac-ethyl.

The fire blight pathogen was injected into the apple shoot at 18 days after the first treatment of growth regulators. By 21 DAT, the infection was obvious in all shoots but the visual rating of fire blight damage did not vary by treatment (see Table 3). By 25 DAT the infection had spread rapidly and treatments where growth suppression was the strongest showed significantly less fire blight damage than the untreated check. Disease severity varied greatly between plants as indicated by the high coefficient of variation values (CV).

As the fire blight spread down the stem the infected stem would become discolored. The length of this discolored tissue was measured as canker length. By 37 DAT, all growth regulator treatments resulted in reduced canker length as compared to the untreated check (see Table 4). In many cases the canker consumed all of the new growth on the shoot and continued to move into the portion of the stem that was form the previous season (2nd year wood). All growth regulator treatments reduced the spread of the infection into second year wood as compare to the untreated check.

Treatments of prohexadione calcium at 100/100 ppm and trinexapac-ethyl at both 500/500 ppm and 1000/1000 ppm reduced the severity and the spread of the fire blight symptoms. Treatments that were most effective at controlling shoot growth were also the most effective treatments in reducing fire blight severity.

EXAMPLE 3

Seedling pears were treated with the growth regulator prohexadione calcium when new shoot growth measured 3–10 cm. A second application of prohexadione calcium was made three weeks later. The application technique was identical to the first application. The prohexadione calcium was applied at 125/125 ppm, 250/250 ppm, 375/375 ppm, 500/500 ppm, and 750/750 ppm active ingredient.

Pear shoots were needle inoculated with the *Erwinia amylovora* pathogen two weeks after the first treatment with prohexadione calcium. New shoot growth was measured at the time of application and weekly until disease symptoms became obvious. The results are displayed in Table 5.

TABLE 5

Pear shoot growth and fireblight canker length following treatment with PROHEXADIONE CALCIUM

| Prohexadione | Growth as % of Untreated | Fire Blight Canker Length (cm) | |
|---|---|---|---|
| Calcium | 20 DAT | 38 DAT | 45 DAT |
| Untreated | 100 | 11 ab | 14 a |
| 125/125 ppm | 52 | 13 a | 13 a |
| 250/250 ppm | 36 | 7 abc | 9 ab |

TABLE 5-continued

Pear shoot growth and fireblight canker length following treatment with PROHEXADIONE CALCIUM

| Prohexadione | Growth as % of Untreated | Fire Blight Canker Length (cm) | |
|---|---|---|---|
| Calcium | 20 DAT | 38 DAT | 45 DAT |
| 375/375 ppm | 19 | 6 bc | 6 b |
| 500/500 ppm | 32 | 8 abc | 9 ab |
| 750/750 ppm | 19 | 4 c | 6 b |
| CV | 45.1 | 59.9 | 54.8 |

Means followed by the same letter are not significantly different (Duncan's MRT, P = .05).

All growth regulator treatments reduced pear shoot growth as compared to the untreated plants. Treatments of prohexadione calcium at 125/125 ppm, 250/250 ppm, 375/375 ppm, 500/500 ppm, and 750/750 ppm tended to reduce the severity and the spread of the fireblight symptoms. Treatments that were most effective at controlling fireblight were the 750/750 ppm and 375/375 ppm treated plants.

The invention has been described with reference to various specific embodiments. However, many variations and modifications may be made while remaining within the scope and spirit of the invention.

What is claimed is:

1. A method for the control of fireblight in a plant comprising applying to a plant an effective amount of an acylcyclohexanedione of the following formula:

(I)

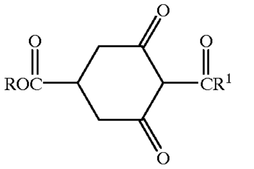

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt or tautomer of said cyclohexane dione compound.

2. The method as recited in claim 1 wherein the said plant is selected from the genera consisting of Cotoneaster, Crataegus, Cydonia, Malus, Photinia, Pyracantha, Pyrus, or Sorbus.

3. The method according to claim 1 wherein the acylcyclohexanedione comprises prohexadione or its pharmacological effective salt.

4. The method according to claim 2 wherein the acylcyclohexanedione comprises prohexadione or its pharmacological effective salt.

5. A method according to claim 3 wherein the salt is calcium.

6. A method according to claim 4 wherein the salt is calcium.

7. The method according to claim 1 wherein the acylcyclohexanedione comprises trinexapac-ethyl.

8. The method according to claim 2 wherein the acylcyclohexanedione comprises trinexapac-ethyl.

9. A method for the control of fireblight in a plant comprising applying to said plant, either in combination or sequentially, an effective amount of prohexadione or its pharmacologically effective salt and an antibiotic.

10. The method as recited in claim 9 wherein the said plant is selected from the genera consisting of Cotoneaster, Crataegus, Cydonia, Malus, Photinia, Pyracantha, Pyrus, or Sorbus.

11. A method for the control of fireblight in a plant comprising applying an effective amount of a compound selected from a compound of the following formula:

(I)

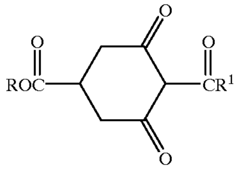

wherein R represents a hydrogen atom or an alkyl group, an alkylthioalkyl group or an unsubstituted or substituted phenyl group; and $R^1$ represents an alkyl group, an unsubstituted or substituted benzyl group, a phenethyl group, a phenoxymethyl group, a 2-thienylmethyl group, an alkoxymethyl group or an alkylthiomethyl group, or a salt of said cyclohexane compound; to the plant.

12. The method as recited in claim 11 wherein the said plant is selected from the genera consisting of Cotoneaster, Crataegus, Cydonia, Malus, Photinia, Pyracantha, Pyrus, or Sorbus.

13. A method for the control of fireblight in a plant comprising applying an effective amount of a compound selected from a compound of the following formula:

(IV)

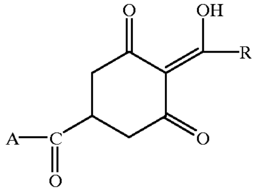

wherein

A is an—$OR_2$ or—$NR_3R_4$ radical,

R is $C_3$–$C_6$ cycloalkyl, $R_2$ $R_3$ and $R_4$ are each independently hydrogen, $C_1$–$C_6$alkyl, $C_1$–$C_6$haloalkyl, $C_2$–$C_{10}$alkoxyalkyl, $C_2$–$C_{10}$alkylthioalkyl, $C_3$–$C_6$alkenyl, which is unsubstituted or substituted by halogen, $C_1$–$C_4$alkoxy or $C_1$–$C_4$alkylthio; $C_3$–$C_6$alkynyl; phenyl or $C_1$–$C_6$aralkyl, wherein the phenyl nucleus is unsubstituted or substituted by halogen, $C_1$–$C_4$alkyl, $C_1$–$C_4$alkoxy, $C_1$–$C_4$haloalkyl, nitro or cyano; one of $R_3$ and $R_4$ is methoxy; or $R_3$ and $R_4$, together with the nitrogen atom to which they are attached, form a 5- or 6-membered heterocyclic ring system which may contain an oxygen or a sulfur atom in the ring; and the metal or ammonium salts thereof; to the plant.

14. The method as recited in claim 13 wherein the said plant is selected from the genera consisting of Cotoneaster, Crataegus, Cydonia, Malus, Photinia, Pyracantha, Pyrus, or Sorbus.

15. The method as recited in claim 2 wherein the said plant is an apple tree.

16. The method as recited in claim 2 wherein the said plant is a pear tree.

17. The method as recited in claim 4 wherein the said plant is an apple tree.

18. The method as recited in claim 4 wherein the said plant is a pear tree.

19. The method as recited in claim 8 wherein the said plant is an apple tree.

20. The method as recited in claim 8 wherein the said plant is a pear tree.

21. The method as recited in claim 10 wherein the said plant is an apple tree.

22. The method as recited in claim 10 wherein the said plant is a pear tree.

23. The method as recited in claim 12 wherein the said plant is an apple tree.

24. The method as recited in claim 12 wherein the said plant is a pear tree.

25. The method as recited in claim 14 wherein the said plant is an apple tree.

26. The method as recited in claim 14 wherein the said plant is a pear tree.

* * * * *